(12) United States Patent
Hansen et al.

(10) Patent No.: US 9,304,055 B2
(45) Date of Patent: *Apr. 5, 2016

(54) SYSTEM AND METHOD FOR IDENTIFICATION OF PIPE DEFECTS THAT LEAK

(71) Applicant: Electro Scan, Inc., Sacramento, CA (US)

(72) Inventors: Charles Hansen, Sacramento, CA (US); Robert Jackson Harris, Rescue, CA (US)

(73) Assignee: Electro Scan, Inc., Sacramento, CA (US)

( * ) Notice: Subject to any disclaimer, the term of this patent is extended or adjusted under 35 U.S.C. 154(b) by 490 days.

This patent is subject to a terminal disclaimer.

(21) Appl. No.: 13/768,949

(22) Filed: Feb. 15, 2013

(65) Prior Publication Data

US 2013/0214786 A1 Aug. 22, 2013

Related U.S. Application Data

(60) Provisional application No. 61/633,810, filed on Feb. 16, 2012, provisional application No. 61/633,811, filed on Feb. 16, 2012, provisional application No. 61/689,248, filed on Jun. 1, 2012.

(51) Int. Cl.
*G01V 3/10* (2006.01)
*G01M 3/40* (2006.01)
*G01N 27/60* (2006.01)
*G01M 5/00* (2006.01)

(52) U.S. Cl.
CPC .............. *G01M 3/40* (2013.01); *G01M 5/0025* (2013.01); *G01M 5/0033* (2013.01); *G01M 5/0083* (2013.01); *G01N 27/60* (2013.01)

(58) Field of Classification Search
CPC ........................................................ G01V 3/10
USPC .......................................................... 324/329
See application file for complete search history.

(56) References Cited

U.S. PATENT DOCUMENTS

| 4,471,651 | A | 9/1984 | Dimeff |
| 6,301,954 | B1 | 10/2001 | Schuberth |
| 7,137,308 | B2 | 11/2006 | Harris |
| 2013/0218485 | A1* | 8/2013 | Hansen et al. ................. 702/38 |

FOREIGN PATENT DOCUMENTS

| JP | 58-055853 | 4/1983 |
| JP | 60-249049 | 12/1985 |

OTHER PUBLICATIONS

Electro Scan FELL 41 or FELL 21, 1 page, 2007.*

* cited by examiner

*Primary Examiner* — Bot Ledynh
(74) *Attorney, Agent, or Firm* — Heisler & Associates

(57) ABSTRACT

The system utilizes electroscan equipment including a voltage source and current meter with a cable having one end grounded and one end having an electric probe thereon sized to fit within an underground pipe. The probe is able to complete an electric circuit back to ground when the probe is adjacent a defect through which electric currents can pass, thus producing varying electric current. A cable reel is provided with portions of the cable supported thereon and with a cable distance sensor coupled to the reel along with the current meter and voltage source in the form of a battery. The current meter and distance sensor transmit wireless signals to an on-site processor, such as a smartphone, for on-site data evaluation. Such unconditioned data is also transmitted to a remote location for conditioning of the data and retransmission of the conditioned data back to the on-site processor.

19 Claims, 5 Drawing Sheets

SYSTEM AND METHOD FOR IDENTIFICATION OF PIPE DEFECTS THAT LEAK

CROSS-REFERENCE TO RELATED APPLICATIONS

This application claims benefit under Title 35, United States Code §119(e) of U.S. Provisional Application No. 61/633,810 filed on Feb. 16, 2012, U.S. Provisional Application No. 61/633,811 filed on Feb. 16, 2012 and U.S. Provisional Application No. 61/689,248 filed on Jun. 1, 2012.

FIELD OF THE INVENTION

The following invention relates to systems and methods for detecting defects in underground pipes, such as sewer pipes or water pipes which have a potential to leak. More particularly, this invention relates to systems and methods which involve establishing if electric current flows between ground adjacent the pipe and an interior of the pipe, which circuit increases in current amplitude when an electric probe passing through a pipe filled with electrically conductive fluid approaches defects in the pipe.

BACKGROUND OF THE INVENTION

Sewer systems and other underground pipes can be difficult to inspect due to their hidden location. Leaks in such pipes can increase costs associated with operating the pipe, and potentially create hazards. Thus, it is beneficial to identify defects in the pipe which can leak (both leaks into and out of the pipe).

One form of defect detection is described in detail in ASTM Standard F2550-06 which describes an electroscan method for defect detection by measuring variations in electric current flow through walls of the pipe as part of a series circuit including a voltage source and an electric current sensor, which collects data as the probe moves through a known position within the pipe.

One such probe beneficial for use in conducting this electroscan is the segmented measuring probe for sewer pipes described in U.S. Pat. No. 6,301,954, incorporated herein by reference in its entirety. Such probes effectively concentrate the electric current over a relatively short length of the pipe in which the probe is located, so that electric current amplitude data gathered by the electroscan method can be accurately correlated with the condition of the pipe directly adjacent the probe.

Operation of the electro scan method can be difficult in that there is a challenge associated with accurately correlating the current amplitude data with the probe position. If the probe is not where the operators think it is when current data is gathered from the current meter, operators will mistakenly associate the current data correlating with pipe defects to the wrong portions of the pipe. Repairs might then be done in the wrong location or further analysis conducted in the wrong location, wasting time, resources and increasing the cost of further analysis and repairs. To precisely correlate probe position with current amplitude data can be a time intensive and laborious process, thus magnifying the resources required to analyze a section of pipe. Accordingly, a need exists for better systems and methods for efficiently gathering and correlating both current amplitude data and probe position data and combining this data into a two-dimensional data array for viewing and meaningful analysis.

Furthermore, raw data gathered from the current meter and probe position often need significant conditioning before it can be most meaningfully evaluated by personnel. Such analysis is beneficially done at a remote location where the most specialized data conditioning software can act on the data, and where the unconditioned and conditioned data can simultaneously be archived and incorporated into a larger data set of overall piping system condition. Data, once conditioned at the remote location, can then be beneficially returned to the site where the operators are located for more precise interpretation of the current amplitude data and correlation to potential pipe defects.

SUMMARY OF THE INVENTION

With this invention a system and method are provided for operating electroscan type pipe defect detection analysis with equipment and methods to enhance the results achieved thereby. The system includes an electric probe coupled to a distal end of an electrically conductive cable also having a proximal end opposite the distal end. The probe is preferably of a type similar to that disclosed in U.S. Pat. No. 6,301,958, incorporated herein by reference in its entirety. A voltage source is provided adjacent to the proximal end of the electrically conductive cable, typically in the form of a battery. An electric meter, typically in the form of a current meter, is also located along the electrically conductive cable, typically near the proximal end thereof.

A ground interface, typically in the form of a ground stake, is penetrated into ground in the general area of the pipe to be inspected and has a ground wire which extends to the proximal end of the electrically conductive cable. Thus, a series electric circuit is created which is closed by passage of electric current from the probe through a defect in the pipe wall and through ground between this defect and the ground interface.

Amplitude of this current in this circuit is measured by the electric meter. Probe position data is also gathered so that the probe position data is correlated with the electric current amplitude to create an unconditioned two-dimensional data set of current amplitude versus probe position.

A cable reel is provided to assist in storing portions of the electrically conductive cable which are not yet drawn down into the pipe. This cable reel also beneficially includes the voltage source and current meter mounted thereto and most preferably rotating along with portions of the cable adjacent the proximal end thereof. The cable is routed through a cable distance sensor which is preferably fixed to a frame of this cable reel and measures an amount of cable played off of the reel and into the pipe extending toward the probe. This cable distance sensor is correlated with probe position so that the position of the probe is known for the current amplitude data.

As the probe is drawn through the pipe being evaluated, the cable plays off of the reel and passes through the cable position sensor. Electric current data is simultaneously gathered. The cable position sensor and electric meter preferably each include transmitters which transmit to a separate on-site portable electronic device, such as in the form of a smartphone. One form of such transmission can be in the form of Bluetooth signals. Signals are received by the smartphone or other on-site processor which correlates the two signals into a single two-dimensional data set of current amplitude versus probe position.

The reel also facilitates effective grounding of the proximal end of the cable by having the proximal end of the cable first grounded to a rotating hub of the reel and having this hub rotate upon an axle sufficiently closely that a grounded electric connection is maintained therebetween. The stationary axle has an end which can have the ground wire of the ground stake electrically coupled thereto so that a ground connection exists between the ground stake and the hub of the reel. The overall system can thus be readily set up and used to support the cable as it is deployed and the probe is drawn through a pipe being evaluated.

Data is automatically transmitted to the smartphone or other portable on-site processor which can then readily gather an unconditioned data set. This data set can be viewed on site, can trigger alarms when preset limits associated with defects of a preselected magnitude are identified. This unconditioned data set can be viewed through the on-site processor, such as a smartphone. The unconditioned data can also be transmitted, such as by cellular data link associated with a smartphone, to a remote location for archiving and conditioning of the data into more meaningful data which can be transmitted back to the on-site processor for display to personnel in the field in near real time. The conditioned data can be incorporated into a larger overall data set for an overall piping system, of which the evaluated pipe is only a portion.

Consistent with the electroscan method to which this invention is directed, other equipment is also utilized such as to maintain a flooded or substantially flooded state within the pipe being evaluated and to accommodate particular situations such as when the pipe to be analyzed is a lateral pipe or a mainline Various different equipment are also known in the art for drawing the probe through the pipe while maintaining this submerged state within the pipe, such as utilization of a haul line such as that associated with a jet cleaner hose, as is known in the art.

OBJECTS OF THE INVENTION

Accordingly, a primary object of the present invention is to provide a system for efficiently and accurately gathering data associated with underground pipe conditions utilizing the electroscan method.

Another object of the present invention is to provide a method and apparatus for gathering, displaying, conditioning and archiving pipe electroscan data for maximum usefulness.

Another object of the present invention is to provide a system and apparatus for evaluating pipe sections in underground locations, such as sewer pipes or water pipes, for defects in the pipe which have the potential to leak.

Another object of the present invention is to minimize leakage of fluids into or out of pipelines by providing an effective method and apparatus for evaluating underground pipe condition.

Another object of the present invention is to provide a system and apparatus for managing cable associated with an electroscan underground pipe evaluation system for convenient and easy operation and to acquire highly precise data.

Another object of the present invention is to provide a system and method for collection, analysis and archiving of pipe defect data which includes both unconditioned data and conditioned data.

Other further objects of the present invention will become apparent from a careful reading of the included drawing figures, the claims and detailed description of the invention.

DESCRIPTION OF THE PREFERRED EMBODIMENT

Figure 1:
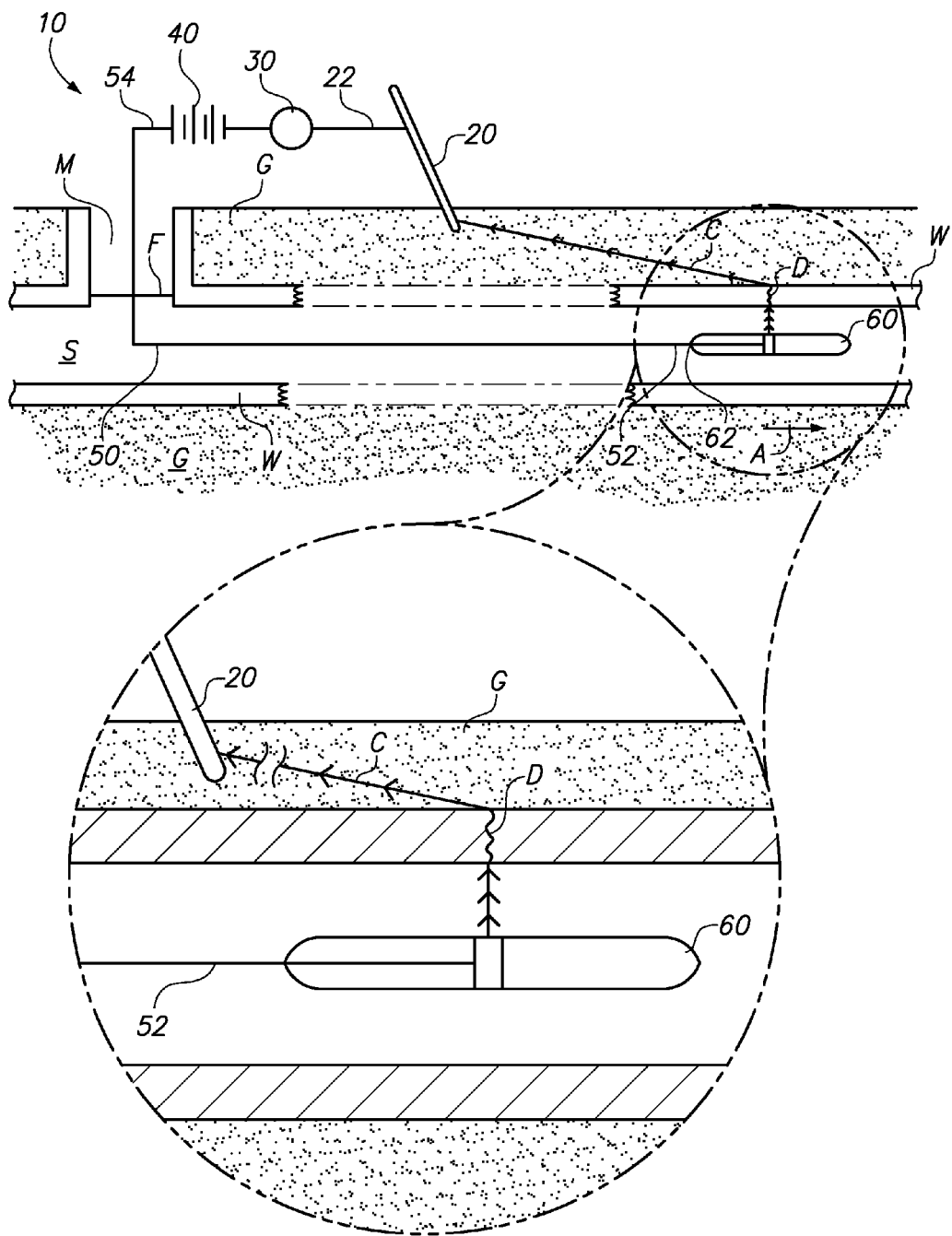
FIG. 1 is a schematic depiction of the prior art electroscan underground pipe defect detection methodology associated with ASTM Standard F2550-06 to which the details of this invention are directed.

Referring to the drawings, wherein like reference numerals represent like parts throughout the various drawing figures, reference numeral 10 is directed to a system for identification of pipe defects. The system 10 (FIG. 1) is consistent with a prior art system described in ASTM (ASTM International, formerly known as "American Society for Testing and Materials") Standard F2550-06 described as "Standard Practice for Locating Leaks in Sewer Pipes Using Electroscan—the Variation of Electric Current Flow Through the Pipe Wall." This system 10 can be utilized in underground pipes such as a sewer S (FIG. 2) by passing a probe 60 through the sewer S pipe, such as between adjacent manholes M to detect defects D in the pipe wall W. The system incorporates a reel assembly 110 (FIGS. 4 and 5) and data handling and processing (FIG. 6) with a smartphone 190 or other on-site processor, as well as a remote processing location 200, for efficient and accurate data handling and overall database construction of pipe condition data.

Figure 2:
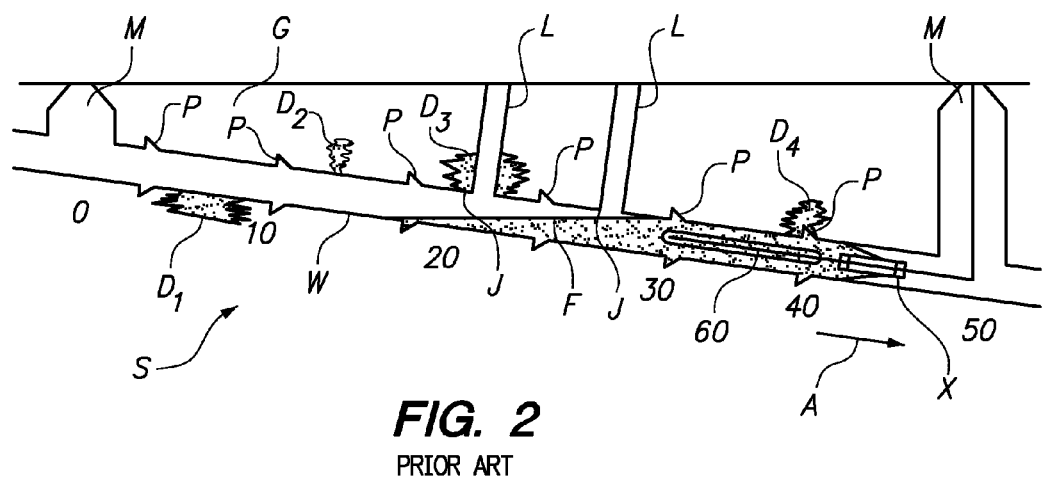
FIG. 2 is a schematic generalized depiction of a section of underground pipe which is undergoing the electroscan evaluation associated with FIG. 1.
Figure 3:
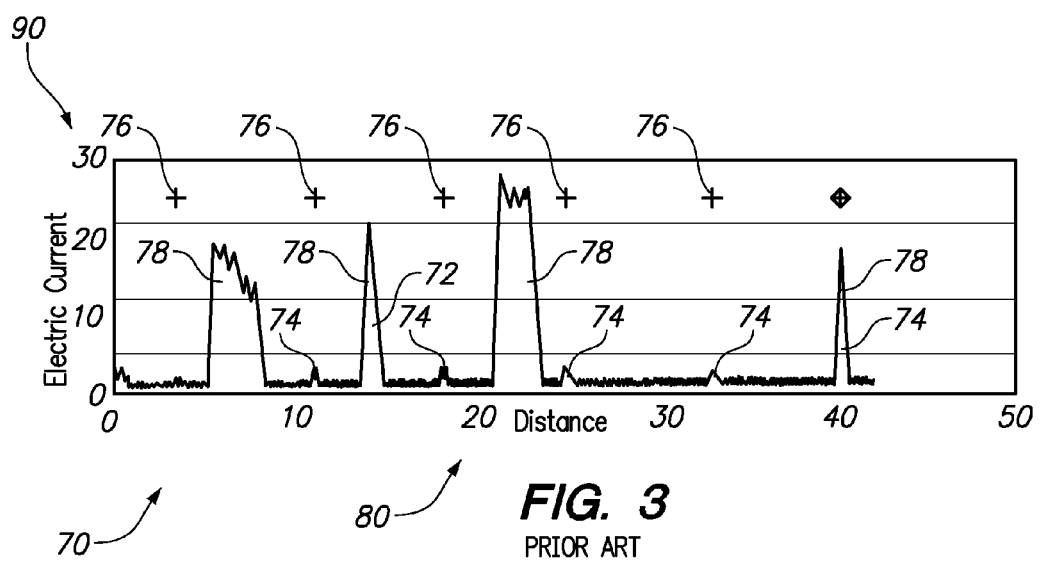
FIG. 3 is a graphic depiction of a typical graph of current amplitude versus probe location as it might appear utilizing the electroscan method associated with FIG. 1 and with current amplitude spikes shown in FIG. 3 correlating with leaks depicted in FIG. 2 and illustrating how current spikes plus shape and area under current spikes indicate presence of defects, size and type of defects in the pipe with a propensity for leaking.

With particular reference to FIGS. 1-3, basic details of the prior art electroscan pipe defect evaluation system are described. This basic electroscan leak detection system 10 causes a series electric circuit to be formed extending along a cable 50 which extends from a probe end 52 to a proximal end 54. The probe end 52 has an electric probe 60 attached thereto, such as through a connector 62. This probe 60 can be similar to or the same as a probe such as that described in U.S. Pat. No. 6,301,954, incorporated herein in its entirety.

The proximal end 54 of the cable 50 is coupled to a ground stake 20. A voltage source 40 is provided along the cable 50. An electric meter, such as in the form of a current meter, is also located along the cable or between the voltage source 40 and the ground stake 20 to measure current within this series circuit. Such location of the voltage source and/or the electric meter can involve physical connection or non-physical, such as involving inductance or electromagnetic field forces. A final portion of the series circuit is in the form of a current path C passing from the ground stake 20, through the ground G, and through a defect D in the pipe wall W and through electrically conductive fluid F (typically water with dissolved electrolytes) contained within the pipe and then to the probe 60.

The current meter 30 detects a small amount of current when the pipe wall W is free of defects, because the pipe wall is typically formed of a low or non-electrically conductive material, such as cement pipe, clay pipe, plastic pipe, etc. When there is a defect in the pipe, and because the pipe is filled with electrically conductive fluid F, fluid will pass through this crack or other defect in the flooded pipe and a current pathway is thus provided to enhance an amount of current detected by the current meter 30 or other electric meter. A size and shape of current spike generally correlates with an amount, size and/or shape of this defect.

With reference to FIGS. 2 and 3, examples of different types of defects are indicated by different sizes, shapes and areas under the curve, and amplitudes of electric current spikes 78 in the data plot 72 of current versus probe 60 position. For instance, a longitudinal crack such as defect $D_1$ (FIG. 2) results in a relatively wide current amplitude spike which is spaced away from the location of any laterals or joints between pipe segments. Small and regularly located increases in electric current amplitude are indicative of pipe joint P locations which under normal circumstances might still allow sufficient fluid F to pass therethrough to create a small spike in current.

Point or radial defects such as depicted by $D_2$ (FIG. 2) tend to provide a narrower spike in current amplitude with less area under the curve (FIG. 3). Defects adjacent a lateral L in the sewer S are depicted by defect $D_3$ (FIG. 2) and generally appear in the graphed data as a wide current amplitude spike which is aligned with a location of the lateral. Finally, defects 78 which are aligned with joint locations in the pipe are indicative of a defective joint such as defect $D_4$ (FIG. 2), and correspondingly depicted in FIG. 3.

Figure 4:
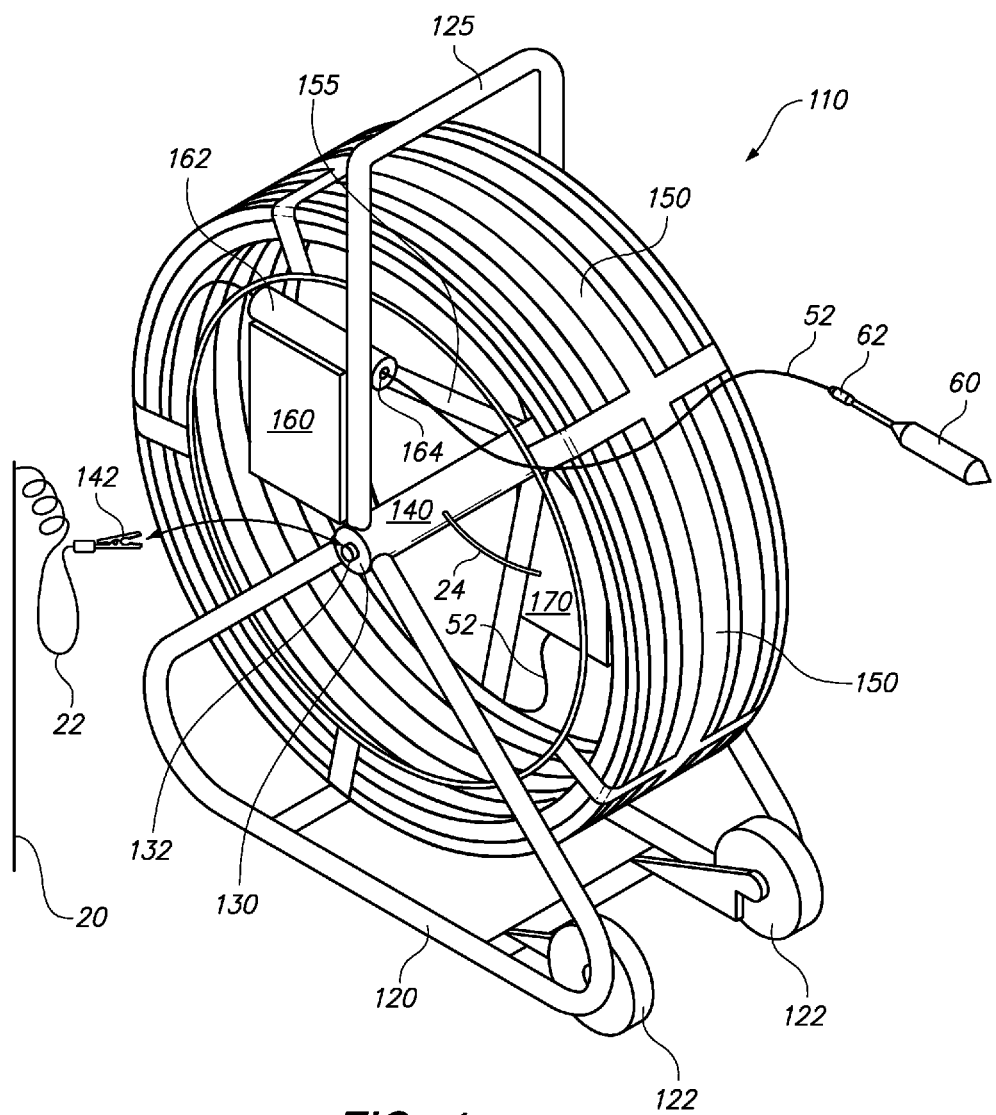
FIG. 4 is a perspective view of a cable reel for use according to a preferred system and method of this invention to enhance accuracy and convenience of operation of the system and method of this invention.
Figure 5:
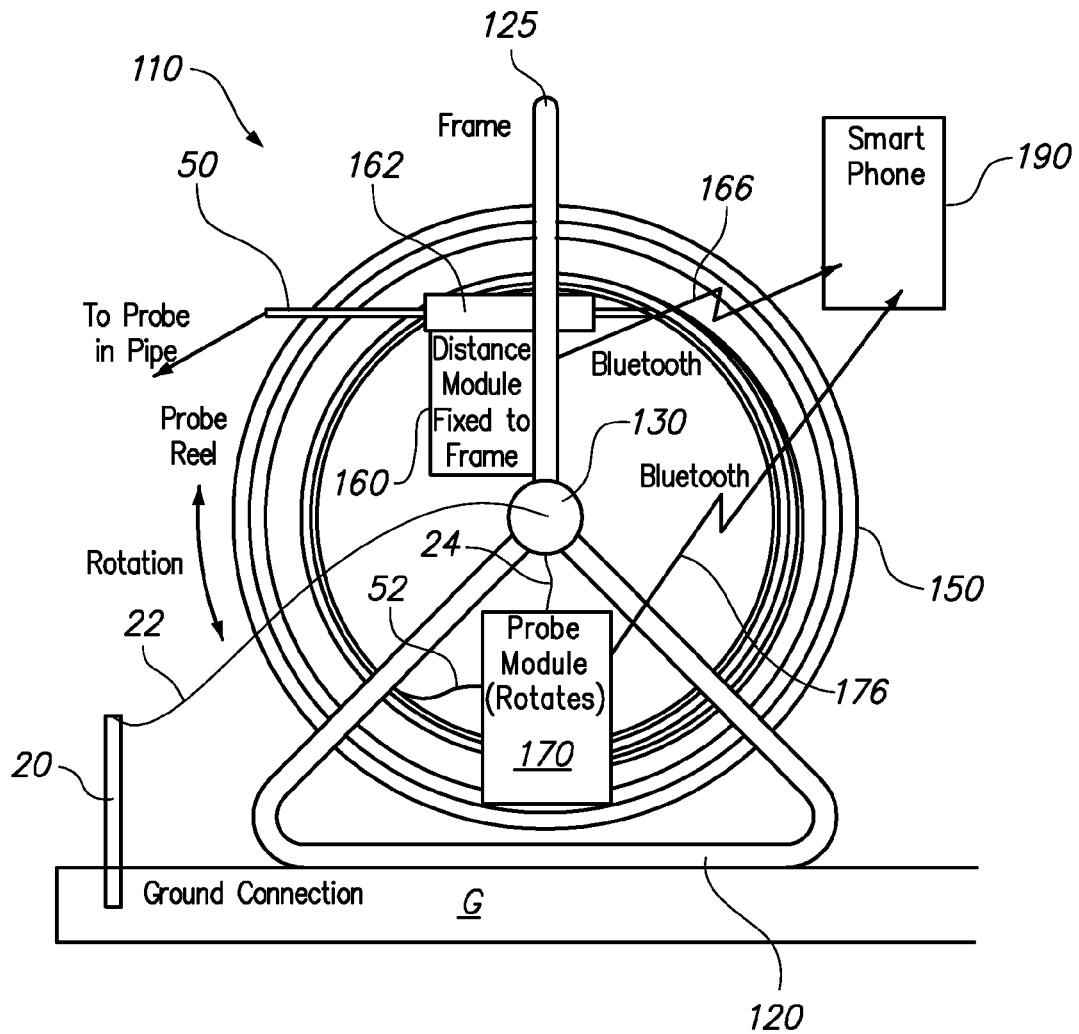
FIG. 5 is a side elevation view of that which is shown in FIG. 4.

In essence, and with particular reference to FIGS. 4 and 5, basic details of the reel assembly 110 of the enhanced implementation of the system 10 of this invention are described, according to a most preferred embodiment. The reel assembly 110 allows for efficiency and accuracy to be improved when implementing the system 10. This reel assembly 110 generally includes a foot 120 which can rest upon the ground. An axle 130 near a center of the reel assembly 110 supports a hub 140 thereon with the axle 130 being stationary and fixed to the foot 120 with the hub 140 rotating upon the axle 130. A cable support cage 150 acts as a form of spool rotating along with the hub upon the axle 130. The cable support cage 150 has a series of turns of the cable 150 adjacent thereto.

A distance module 160 is preferably fixedly mounted to the reel assembly 110, such as to portions of the structure extending up from the foot 120. This distance module 160 is configured to accurately measure an amount of cable 50 played off of the reel assembly 110. A probe module 170 is also mounted to the reel assembly 110, but to a portion thereof which rotates along with the cable support cage 150 and portions of the cable 50 mounted upon the cable support cage 150. This probe module 170 preferably includes the voltage source 40 such as in the form of a battery and the electric meter 30, such as in the form of a current meter thereon. Both the distance module 160 and probe module 170 preferably include transmitters 166, 176 so that data collected thereby can be transmitted to a common smartphone 190 or other on-site processor where these signals can be correlated together into a single unconditioned data set. The smartphone 190 can transmit this unconditioned data to a remote processing location 200 (FIG. 6), such as over a cellular data network, where the data can be conditioned, archived and added to an overall piping evaluation database, and also can be transmitted back to the field in near real time for analysis by operators at the pipeline evaluation location.

More specifically, and with continuing reference to FIGS. 4 and 5, particular details of the reel assembly 110 are described, according to this most preferred embodiment. The reel assembly 110 includes a fixed frame portion and a rotating portion which rotates relative to the fixed portion. The fixed portion includes the foot 120 adapted to rest upon the ground. A handle 125 extends up from the foot 120 and is conveniently located to grip and carry the reel assembly 110 without having to grip rotating portions of the reel assembly 110. Wheels 122 can optionally be provided on portions of the foot 120 to allow for rolling of the reel assembly 110 on the ground, especially when a large amount of cable 150 is supported on the reel assembly 110.

The rigid frame portion of the reel assembly 110 also supports an axle 130 at a junction between the handle 125 and the foot 120. This axle 130 extends along a centerline of rotation of rotating portions of the reel assembly 110. The axle 130 acts as a shaft about which a hub 140 of rotating portions of the reel assembly 110 can be supported in a rotating fashion. Preferably, the axle 130 has ends 134 which either extend out from other portions of the fixed frame somewhat or are otherwise configured to be conveniently accessed for attachment through a ground clip 142. This ground clip 142 extends to a ground wire 22 which extends to the ground stake 20. In this way, the axle 130 of the reel assembly 110 is grounded effectively to the ground stake 20.

Rotating portions of the reel assembly 110 are all supported by fixed portions of the reel assembly 110 through the hub 140. The hub 140 is a hollow cylinder with the axle 130 passing through a central portion thereof and along a centerline of the hub 140. A cable support cage 150 is oriented circumferentially about the hub 140 with spokes 155 supporting the cable support cage 150 from the hub 140. This cable support cage 150 is preferably largely open so that cable 50 supported thereon can be readily cleaned and can readily dry, but has sufficient support to keep it from falling off of the cable support cage 150, which acts as a form of spool for the cable 50.

The reel assembly 110 preferably includes a distance module 160 and probe module 170 affixed thereto to conveniently allow for gathering and collection of accurate current (or other electric parameter) amplitude and probe position data. The distance module 160 is preferably mounted to fixed portions of the reel assembly 110, such as to portions of the handle 125 or foot 120. This distance module 160 is preferably in the for of a box which is rigidly attached to the reel assembly 110 and has a cable sleeve 162 with a bore passing therethrough on a portion thereof. The cable 50 is routed through this bore 164 in the cable sleeve 162.

A detector is located adjacent this bore 164 which can measure an amount of cable passing through the cable sleeve 162. In one form, this detector is in the form of a rolling dial which extends sufficiently laterally into the bore 164 so that the cable 50 cannot pass through the bore 164 unless it causes this wheel to rotate. A rotational transducer is associated with this wheel so that it measures a number of turns of the wheel and correlates this number of turns with an amount of cable 50 played off of the reel assembly 110.

Initially, an operator will measure precisely a distance from the distance module 160 to a manhole M and down to a bottom of the manhole M to a start location within the pipe to be evaluated, and can enter this "offset" into the on-site processor if desired. Then, as distance data is collected associated with the cable 50 passing through the bore 164 in the distance module 160, this distance data is correlated with distance away from this start point below the entry manhole for the cable. The distance module 160 can include an input device where this start distance can be entered. As an alternative, the distance module 160 can merely include a zeroing button which can be depressed when the probe 60 is seen to be at the start location and the cable 50 is generally taut between the location of the reel assembly 110 and the input manhole M.

While the reel assembly 110 preferably does not move during pipe evaluation, should the reel assembly 110 move, or should slack develop in the cable 50, which would cause distance data from the distance module 160 to come out of correlation with the position of the probe 60, such potential errors can be corrected during conditioning of the data, such as at the remote processing location 200. One form of such conditioning involves identifying small spikes in current amplitude data correlating with joints in the pipe. When a distance between joints in the pipe is already known, such relatively small errors in distance data and probe location data can be corrected by causing detected current spikes associated with joints to control rather than actual measured distance data from the distance module 160.

The on-site processor is provided for initial collection of data from the distance module 160. This on-site processor is preferably in the form of a smartphone 190. While the distance module 160 could be hard wired to the smartphone 190 or other on-site processor, most preferably a wireless transmitter is associated with the distance module 160. This wireless transmitter 166 transmits distance data to the smartphone 190. The distance data can be given a timestamp or can otherwise be correlated with current amplitude data from the probe module 170. In one form this transmitter 166 is a Bluetooth transmitter and the smartphone 190 is a Bluetooth enabled smartphone.

Preferably, a dedicated frequency is provided for the distance module 160 so that the transmitter 166 avoids interference when communicating with the smartphone 190. A data sample rate can be provided by the distance module 160 and associated software operating on the smartphone 190 depending on the sensitivity desired for the operation of the overall system 10.

The probe module 170 includes the electric current meter (or other electric parameter meter) thereon and preferably also the voltage source 40, such as in the form of a battery. Most preferably, these elements, including the electric meter 30 and voltage source 40, are located within the probe module 170 which are mounted to a rotating portion of the reel assembly 110, such as to spokes 155 between the cable support cage 150 and the hub 140. In this way, the voltage source 40 can be located with nothing but electric cable 50 extending from the voltage source 40 to the probe 60, and to minimize any distortions which might come from poor connections within the overall circuit.

The current meter 30 is also preferably provided with this probe module 170 and rotating with the cable support cage 150 and hub 140, so that the current meter can be intimately coupled to the cable 50 and measure current passing through the cable 50 and associated portions of the overall series circuit. While this location is desirable, it is conceivable that other portions of the series circuit could have the electric meter 30 located thereon. By utilizing a battery for the voltage source 40, no rotating connection is required, such as brushes to provide electric power to drive the series circuit associated with the system 10.

The probe module 170 preferably includes a transmitter 176 which can transmit electric current data from the electric current sensor 30 directly to the smartphone 190 or other on-site processor. This transmitter 176 transmits a current amplitude signal which correlates with a character of defects located within the pipe wall W adjacent the probe 60. This current amplitude data is preferably transmitted by Bluetooth to the smartphone 190. The current amplitude data is transmitted in a manner which allows it to be correlated with probe location/distance data from the distance module 160, such as by providing a time stamp associated with the current amplitude data. Other forms of transmission other than Bluetooth could be utilized by the transmitter 176.

The smartphone 190 or other on-site processor analyzes the two signals, one from the distance module 160 and one from the probe module 170 and correlates each signal so that a resulting unconditioned two-dimensional data set is created which has a probe position field and a corresponding current amplitude field. This two-dimensional data set can be graphed such as in the form of current amplitude versus distance (see FIG. 3) and provide an indication of where defects might exist. As an alternative to time stamps, a data set can merely be created in real time from the two signals received by the on-site processor. As the data is typically sent in packets, the elapsed time between packets can also be used to correlate the two data sets together.

Initially, this data is unconditioned data. For instance, it does not take into account the conductivity of the soil. Also, it has not been conditioned to factor in any slack or other irregularities in playing out of the cable 50 which might cause probe position data to require adjustment, such as utilizing joint position data to correct the distance portion of the signal. While this unconditioned data is less precise, there is some benefit in displaying this unconditioned data through the on-site processor, such as a smartphone, such as on the display of the smartphone. For instance, such display can verify that data is being gathered. A skilled technician might be able to tell whether the data will be useful once conditioned or if something is wrong with the operation of the system. Also, when extreme conditions exist such as an exceptionally large defect, even unconditioned data would tend to clearly show such a defect. Alarms can be preset into the smartphone which would indicate to even untrained personnel a high likelihood of a serious defect and the approximate location of the defect, such that further remedial action can immediately be taken if necessary.

Figure 6:
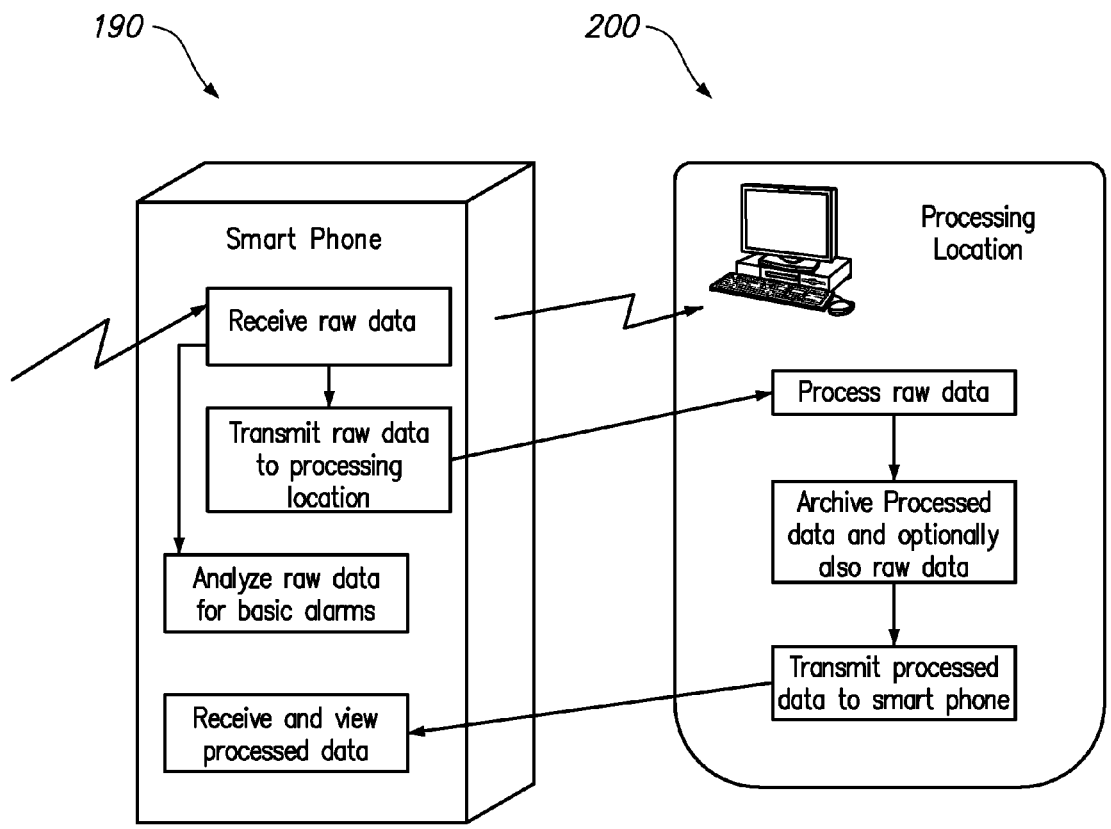
FIG. 6 is a schematic depicting an on-site processor in the form of a smartphone in a preferred embodiment communicating with a remote processing location and illustrating how unconditioned raw data is received by the smartphone, can potentially be displayed and also is transmitted to the remote processing location for conditioning, archiving and potentially retransmission back to the smartphone for further analysis of conditioned data by personnel at the pipe evaluation site.

With particular reference to FIG. 6, further conditioning and other handling of the unconditioned data and later processed and conditioned data are described. The unconditioned or raw data is initially received by the smartphone, typically in the form of two separate transmissions from the distance module and the probe module which are correlated together in a single unconditioned signal. The smartphone 190 preferably communicates with a remote processing location 200, such as through utilizing a cellular data transmission system built into the smartphone 190, or utilizing other transmission techniques for other forms of on-site processors. Once this raw data has been transmitted to the processing location, the raw data can be archived in raw form. The raw data can also be conditioned, such as to normalize the current amplitude data. For instance, different soil conductivity conditions will result in different magnitudes of current being measured by the current sensor 30. Also, the conductivity of the fluid F within the pipe will have an effect on the magnitude of the current measured by the current meter 30. These current amplitude varying effects will tend to be constant along the entire length of pipe being examined and so do not totally obscure spikes in current amplitude associated with a defect that could leak. However, without conditioning, these spikes in the data can be somewhat obscured and more difficult to identify and properly interpret.

One form of current amplitude normalization involves finding the highest or near highest reading of current amplitude and giving it an arbitrary value, such as one hundred percent. All other current amplitude data is compared to this greatest amplitude data to identify a percentage that each current amplitude data set bears relative to this highest amplitude. A current amplitude reading that is ninety percent of the maximum would be given a value of "ninety." In this way, the data set would be normalized in a linear fashion. In some instances, non-linear normalization might be more effective such as utilizing a logarithmic scale rather than a linear scale or some other form of normalization. For instance, statistical variation away from a norm, in the form of standard deviations, might be utilized. By utilizing common current amplitude normalization techniques and having field experience in the defects actually exhibited, the best current normalization techniques can be developed and implemented.

Data conditioning can also involve corrections in the distance signal provided from the distance module 160. For instance, and as discussed above, the position of joints P between known segments of pipes can be seen within the current amplitude data as a form of regular small spikes. The expected location of these small spikes can be compared to the actual location that they are plotted utilizing original distance module signal data. If they are out of synch with each other, this can indicate stretching in the cable 160, accumulated distance errors associated with poor calibration of the sensor in the distance module 160, bends in the pipe being evaluated, causing the cable to travel a distance slightly greater than or less than an actual length of the pipe, or excessive or varying slack in portions of the cable 50, and particularly between the reel assembly 110 and a first manhole where the cable 50 enters the pipe. Data conditioning can involve correcting the actual measured distance coordinate to line up with the joint indicative current amplitude spikes, to properly locate the current amplitude spikes that might be indicative of defects in the pipe.

Other conditioning can also occur, such as to eliminate static or noise from the data or to eliminate potential forms of interference from the data. The conditioned data can be archived similar to the way that the unconditioned data is archived. The conditioned data can also be utilized with other conditioned data within a larger overall database of an overall piping network, such as an overall sewer system, so that a sewer operator or other underground pipeline operator can have a characterization of the status of the overall pipeline system, which can act as a benchmark when future testing is performed and to compare the relative health of different portions of the system to each other.

Finally, the conditioned data can be transmitted back to the remote processor, such as a smartphone 190. This conditioned data can be displayed on the smartphone 190 or other display associated with the on-site processor so that field personnel can see the now conditioned data. The conditioning process can be automated and occur quickly so that this retransmission of the conditioned data can occur in near real time. In this way, field personnel can immediately have access to conditioned data which can be viewed and provide the on-site personnel with information such as whether sections of the pipe need to be re-evaluated, or if any serious defects exist which require further inspection by other means, or to provide confidence that accurate data has been gathered before the scanning operation is wrapped up.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for identification of underground pipe defects that leak, comprising in combination:
   an electric probe sized to fit within an underground pipe;
   an electrically conductive cable having a proximal end and a distal end said distal end electrically attached to said probe;
   a voltage source coupled to said cable and spaced from said probe;
   a ground interface coupled to said proximal end of said cable;
   an electric meter positioned to measure an electric signal in a circuit including said cable, said voltage source and said ground interface, said electric signal correlating with defects in the pipe adjacent to said probe;
   a cable reel with at least a portion of said cable located thereon, said cable reel adapted to rotate, said cable reel having said cable simultaneously electrically connected to said ground interface through said proximal end of said cable and electrically connected to said electric probe through said distal end of said cable deployed off of said reel; and
   wherein said cable reel includes a distance sensor adapted to measure a distance that said cable has been extended into the pipe in which said probe is located and to generate a signal correlating with a position of said probe.

2. The system of claim 1 wherein said voltage source includes a battery.

3. The system of claim 2 wherein said electric meter includes a current meter adapted to measure electric current through said cable driven by a voltage produced by said battery.

4. The system of claim 3 wherein said probe, said cable and said battery form a series electric circuit along with said ground interface and a current path extending from said ground interface to said probe, said current path including passage through ground in which said ground interface is located and passing through at least a portion of a pipe in which said probe is located.

5. The system of claim 4 wherein said battery is located on a portion of said reel that rotates relative to a fixed portion.

6. The system of claim 5 wherein said current meter is located on a portion of said reel that rotates, said current meter coupled to a wireless transmitter adapted to transmit a signal wirelessly from said current meter, which signal correlates with defects in the pipe adjacent said probe, said transmitter transmitting said signal to a portable receiver device with a display adapted to present data correlating with said signal.

7. The system of claim 6 wherein said display includes a graph of current amplitude versus distance along the pipe in which said probe is located.

8. The system of claim 7 wherein said portable device is a handheld smartphone.

9. The system of claim 8 wherein said reel includes a distance sensor, said distance sensor fixed to a frame of said reel which remains fixed relative to rotating portions of said reel upon which said proximal end of said cable is mounted, said distance sensor adapted to detect an amount of cable played off of said reel, said distance sensor coupled to a transmitter adapted to transmit a signal to said portable receiver device for correlation of distance data associated with the position of said probe along with current amplitude data for presentation by said display of said portable receiver device.

10. The system of claim 1 wherein said distance sensor is mounted to a frame of said cable reel which remains fixed relative to portions of said reel which rotate and which contain portions of said electrically conductive cable thereon.

11. The system of claim 10 wherein said distance sensor includes a tube with a bore passing therethrough and with said electrically conductive cable routed through said bore, said tube having a detector associated therewith adapted to measure an amount of cable which passes through said tube and past said detector.

12. The system of claim 1 wherein said distance sensor includes a transmitter thereon, said transmitter adapted to transmit a signal correlating with cable distance and probe position to a portable receiver device having a display associated therewith, said portable receiver device including a processor capable of correlating distance sensor data with data from said electric meter for display of sensed electric amplitude versus probe position in a graph.

13. A system for identification of underground pipe defects that leak, comprising in combination:
   an electric probe sized to fit within an underground pipe;
   an electrically conductive cable having a proximal end and a distal end said distal end electrically attached to said probe;
   a voltage source coupled to said cable and spaced from said probe;
   a ground interface coupled to said proximal end of said cable;
   an electric meter positioned to measure an electric signal in a circuit including said cable, said voltage source and said ground interface, said electric signal correlating with defects in the pipe adjacent to said probe;
   a cable reel with at least a portion of said cable located thereon, said cable reel adapted to rotate, said cable reel having said cable simultaneously electrically connected to said ground interface through said proximal end of said cable and electrically connected to said electric probe through said distal end of said cable deployed off of said reel; and
   wherein said cable reel includes a hub with said proximal end of said cable electrically grounded to said hub, said ground stake grounded to said hub with rotation facilitated between said ground stake and said hub while maintaining electric connection.

14. The system of claim 13 wherein said ground stake is coupled to a ground wire having a removable electrical connector at an end thereof opposite said ground stake, said removable electrical connector adapted to be coupled to an end of an axle upon which said hub rotates, said axle and said hub formed of electrically conductive material and with said hub rotating upon said axle in a manner maintaining an electrical connection between said hub and said axle such that said hub is grounded through said axle, through said ground wire and through said ground stake while allowing rotation of said hub relative to said axle.

15. A method for identification of underground pipe defects that leak, including the steps of:
   providing an electric probe sized to fit within an underground pipe, an electrically conductive cable having a proximal end and a distal end, the distal end electrically attached to the probe, a voltage source coupled to the cable and spaced from the probe, a ground interface coupled to the proximal end of the cable, an electric meter positioned to measure an electric signal in a circuit including the cable, the voltage source and the ground interface, the electric signal correlating with defects in the pipe adjacent to the probe, and a cable reel with at least a portion of the cable located thereon, the cable reel adapted to rotate, the cable reel having the cable simultaneously electrically connected to the ground interface through the proximal end of the cable and electrically connected to the electric probe through the distal end of the cable deployed off of the reel;
   measuring an amount of cable played off of the reel correlating with a position of the probe within the pipe; and
   graphing electric signal data from the electric meter versus position data for the probe for visual representation of underground pipe defects.

16. The method of claim 15 wherein said providing step includes providing the voltage source as a battery and said electric meter as a current meter, with a series circuit existing between said electrically conductive cable, the electric probe, the voltage source and the ground interface, as well as at least a portion of ground in which the ground interface is located and a portion of pipe adjacent the probe.

17. The method of claim 15 wherein said measuring step includes providing a cable distance sensor mounted to a fixed frame of the cable reel including a tube with a bore passing therethrough and with the cable routed through the tube such that cable played off of the reel passes through the tube for detecting of an amount of cable passing therethrough.

18. The method of claim 17 wherein the electric meter and the distance sensor each include a wireless transmitter; and
   transmitting signals from said distance sensor and said electric meter to a portable electronic device including a display for graphic presentation of electric amplitude versus probe position by combining probe position data from the distance sensor with electric amplitude data from the electric meter.

19. The method of claim 18 wherein said portable electronic device is a smartphone.

* * * * *